(12) United States Patent
Ruda et al.

(10) Patent No.: US 7,733,482 B2
(45) Date of Patent: Jun. 8, 2010

(54) SYSTEM AND METHOD FOR DETERMINING AT LEAST ONE CONSTITUENT IN AN AMBIENT GAS USING A MICROSYSTEM GAS SENSOR

(76) Inventors: Harry E. Ruda, 21 Brookfield Road, Toronto (CA) M2P 1B1; Carlos Fernandes, 258 Dunn Avenue, Toronto (CA) M6K 2R9

( * ) Notice: Subject to any disclaimer, the term of this patent is extended or adjusted under 35 U.S.C. 154(b) by 198 days.

(21) Appl. No.: 11/691,279

(22) Filed: Mar. 26, 2007

(65) Prior Publication Data

US 2008/0239309 A1     Oct. 2, 2008

(51) Int. Cl.
*G01J 3/30* (2006.01)
(52) U.S. Cl. ..................................... 356/316
(58) Field of Classification Search ............... 356/316
See application file for complete search history.

(56) References Cited

U.S. PATENT DOCUMENTS

| | | | |
|---|---|---|---|
| 5,841,531 A | 11/1998 | Gliddon | |
| 6,366,346 B1 | 4/2002 | Nowak et al. | |
| 6,429,935 B1 * | 8/2002 | Duan | 356/316 |
| 6,851,413 B1 | 2/2005 | Tamol et al. | |
| 6,921,906 B2 | 7/2005 | Hartley et al. | |
| 7,123,361 B1 * | 10/2006 | Doughty | 356/316 |
| 2005/0195393 A1 * | 9/2005 | Karanassios | 356/316 |
| 2007/0273384 A1 * | 11/2007 | Sheverev | 324/464 |

OTHER PUBLICATIONS

International Search Report Dated Jul. 25, 2008 for International Application No. PCT/US08/03916.
Krum and Horvitz, "Locadio: Inferring Motion and Location from Wi-Fi Signal Strengths"; Mobiquitous 2004, Aug. 2004, pp. 4-13.
Anderson and Muller, "Practical Activity Recognition Using GSM Data", Department of Computer Science, University of Bristol, Jul. 2006.
Anderson and Muller, "Context Awareness via GSM Signal Strength Fluctuation", Late Breaking Results, pp. 27-31, May 2006.

(Continued)

*Primary Examiner*—Tarifur Chowdhury
*Assistant Examiner*—Abdullahi Nur
(74) *Attorney, Agent, or Firm*—Hunton & Williams LLP (57) ABSTRACT

A system and method for measuring air quality using a micro-optical mechanical gas sensor is disclosed. According to one embodiment of the present invention, the system includes an emission source that includes a conduit gap for receiving a gas; a plurality of electrodes for applying an electric field to at least a portion of the conduit gap, the application of the electric field creating a plasma in the conduit gap; and a detector that detects an emission from the plasma. The emission source and the detector may be micro-optical mechanical devices. A method for measuring air quality is discloses. According to one embodiment, the method includes the steps of (1) placing a chip containing an emission source and a detector in a gas flow; (2) applying an electric field to at least a portion of a conduit gap within the emission source, the electric field creating a plasma; (3) detecting an emission from the plasma; and (4) processing data related to the detected emission to determine at least one constituent of the gas flow.

21 Claims, 7 Drawing Sheets

OTHER PUBLICATIONS

Sohn, et al, "Mobility Detection Using Everyday GSM Traces", Ubicomp, Sep. 2006.
Anderson and Muller, "Practical Context Awareness for GSM Cell Phones", International Symposium on Wearable Computing (2006) pp. 127-128, Oct. 2006.
Maitland, et al., Increasing the Awareness of Daily Activity Levels With Pervasive Computing, 1st Intern'l Conf. On Pervasive Computing Technologies For Healthcare (Nov. 2006.
Randell and Muller, "Context Awareness by Analysing Accelerometer Data", Department of Computer Science, University of Bristol, 2000.
Lee and Mase, "Activity and Location REcognition Using Wearable Sensors", Pervasive Computing, 2002.
Anderson and Muller, "Exploring GSM Signal Strength Levels in Pervasive Environments", Dept. of Computer Sciences, University of Bristol, 2006.
Patterson, et al., "Inferring High-Level Behaviour From Low-Level Sensors", University of Washington, Dept. of Computer Science and Engineering, 2003.
Kolie, et al., "Activity Zones for Context-Aware Computing", MIT Computer Science and Artificial Intelligence Laboratory, 2003.
Lukowicz, et al., "Recognizing Workshop Activity Using Body Worn Microphones and Accelerometers", ETH-Swiss Federal Institute of Technology, 2003.
Bahl and Padmanabhan, "RADAR: An In-Building RF-Based Computing Applications", Dec. 7, 2001.
Siewiorek, et al., "SenSay: A Contex-Aware Mobile Phone", Human Computer Interaction Institue and Institute For Complex Engineering Systems, Carnegie Mellon University, 2003.
Otsason, et al., "Accurate GSM Indoor Localization", Tartu University/University of Toronto/Intel Research Seattle, 2005.
Devai and Dunn, "Real-Time Motion Classification For Wearable Computing Applicaitons", Dec. 7, 2001.

* cited by examiner

SYSTEM AND METHOD FOR DETERMINING AT LEAST ONE CONSTITUENT IN AN AMBIENT GAS USING A MICROSYSTEM GAS SENSOR

BACKGROUND OF THE INVENTION

1. Field of the Invention

The present invention generally relates to measuring air quality using a sensor, and, more particularly, to a system and method for measuring air quality using a micro-optical mechanical gas sensor.

2. Description of the Related Art

There is growing public awareness and concern about the adverse effects of indoor air quality on human health and productivity in public buildings, work places and personal dwellings. Media attention concerning toxic mold and related health effects as well as the outbreak of infectious diseases such as SARS has led to renewed attention to indoor air quality in homes, commercial buildings, schools and hospitals. See Instrument Society of America (ISA), "Air-Pollution Sensors Forecast 25% Growth by 2003", InTech, September, 1999.

Current commercial air quality monitoring devices are large expensive analytical instruments, such as mass spectrometers and spectroscopes, that are often restricted to monitoring a small number of atmospheric pollutants. Each type of device has its advantage and disadvantages. For example, optical absorption spectroscopy devices are sensitive and selective, but are expensive and non-robust. Electrochemical/electroadsorptive devices, although inexpensive and portable, typically are limited to sensing only one gas. Mass spectroscopy devices are sensitive, but are expensive and requires vacuum technology. Finally, chromatography devices are sensitive, but expensive, non-portable, and non-robust.

A variety of methods are available for simultaneously detecting a number of components in a gas mixture. For example, Raman spectroscopy, Fourier Transform Infrared ("FTIR") spectroscopy, and mass spectroscopy may be used. While these methods have their merits, they also have their drawbacks. Cumbersome vacuum technology, an essential part of mass spectroscopy, limits its portability. FTIR spectroscopy typically employs absorption spectroscopy, which, in order to achieve high sensitivity, requires the use of some form of White cell, see White, J. U., *J. Opt. Soc. Am.* 32,285 (1942), where pathlengths of up to kilometers may be attained. See Hanst, P. L., "Pollution: Trace Gas Analysis" in "Fourier Transform Infrared Spectroscopy", etd. J. R. Ferraro & L. J. Basile, vol. 2, 79-110, Academic Press, Inc. (1979). The use of some form of White cell restricts ruggedness since careful alignment of the infrared beam entering and leaving the cell is required.

SUMMARY OF THE INVENTION

A system and method for measuring air quality using a micro-optical mechanical gas sensor is disclosed. According to one embodiment of the present invention, the system includes an emission source that includes a conduit gap for receiving a gas; a plurality of electrodes for applying an electric field to at least a portion of the conduit gap, the application of the electric field creating a plasma in the conduit gap; and a detector that detects an emission from the plasma. The emission source and the detector may be micro-optical mechanical devices.

According to one embodiment, the width of the conduit gap is less than 100 microns. In another embodiment, the width of the conduit gap is less than 10 microns.

The detector may be an optical detector, a charge coupled device, a photodiode, or a spectrometer. The emission source and the detector may be located on the same chip.

In one embodiment, the emission source may also include partially transmitting mirrors in the conduit gap. In another embodiment, the emission source may include a spacer having a passage within the conduit gap.

The system may include a controller that controls the emission source and the detector. The controller may receive and process signals from the detector.

A method for measuring air quality is discloses. According to one embodiment, the method includes the steps of (1) placing a chip containing an emission source and a detector in a gas flow; (2) applying an electric field to at least a portion of a conduit gap within the emission source, the electric field creating a plasma; (3) detecting an emission from the plasma; and (4) processing data related to the detected emission to determine at least one constituent of the gas flow.

According to one embodiment, the width of the conduit gap is less than 100 microns. In another embodiment, the width of the conduit gap is less than 10 microns.

The emission source and the detector may be micro-optical mechanical devices.

The step of detecting an emission from the plasma may include the step of detecting the emission with at least one of an optical detector, a charge coupled device, a photodiode, and a spectrometer.

The method may also include the step of altering a strength of the electric field based on the detected emission.

The method may further include the step of displaying an identity of the at least one constituent.

According to another embodiment, a system for measuring air quality is disclosed. The system includes a controller and a plurality of micro-optical mechanical sensor in communication with the controller. Each micro-optical mechanical sensor may include an emission source having a conduit gap for receiving a gas, a plurality of electrodes for applying an electric field to at least a portion of the conduit gap, the application of the electric field creating a plasma in the conduit gap, and a detector that detects an emission from the plasma.

According to one embodiment, the width of the conduit gap is less than 100 microns. In another embodiment, the width of the conduit gap is less than 10 microns.

The detector may be an optical detector, a charge coupled device, a photodiode, or a spectrometer. The emission source and the detector may be located on the same chip.

It is a technical advantage that a system and method for measuring air quality using micro-optical mechanical gas sensor are disclosed. It is another technical advantage that the system may include an emission source and a detector that may be micro-optical mechanical devices. It is another technical advantage that the emission source may include a conduit gap, and the width of the conduit gap is less than 100 microns.

BRIEF DESCRIPTION OF THE DRAWINGS

For a more complete understanding of the present invention, the objects and advantages thereof, reference is now made to the following descriptions taken in connection with the accompanying drawings in which.

DETAILED DESCRIPTION OF PREFERRED EMBODIMENTS

Preferred embodiments of the present invention and their advantages may be understood by referring to FIGS. 1-6, wherein like reference numerals refer to like elements.

In order to employ the attractive features of compactness, portability, sensitivity and robustness in a single, integrated platform, the present invention includes a micro-optical mechanical ("MOMS")-based device for real-time monitoring of a variety of chemical species in the atmosphere. According to one embodiment of the present invention, the core of the device is a gas sensor that employs emission spectroscopy integrated with a direct current glow discharge as the emission source.

Figure 1:
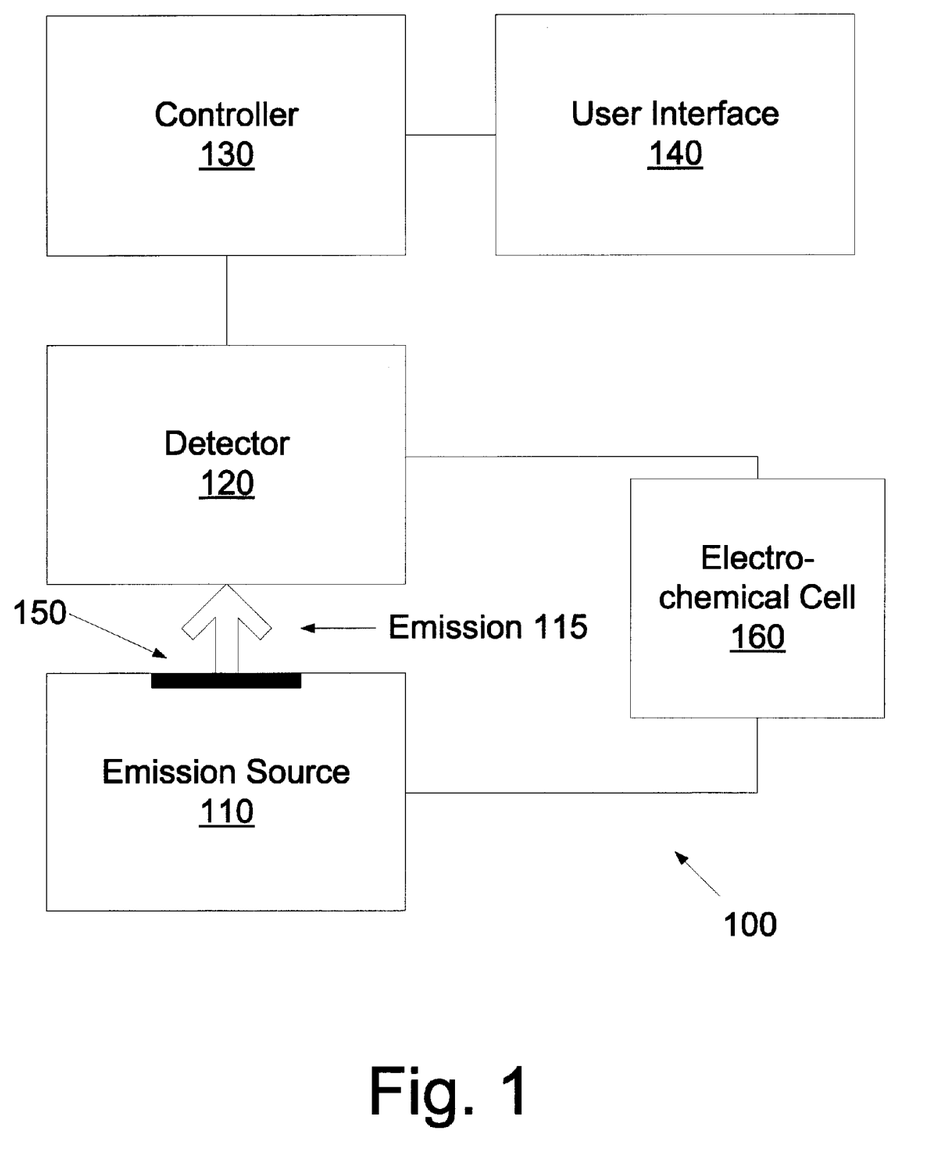
FIG. 1 is a block diagram of the system for measuring air quality using micro-optical mechanical gas sensor according to one embodiment of the present invention.

Referring to FIG. 1, a block diagram of a system for measuring air quality using micro-optical mechanical gas sensor is provided. According to one embodiment of the present invention, the system includes four general components: emission source 110, detector 120, controller 130, and user interface 140. In general, emission source 110 produces light emission 115 that is detected by detector 120. Controller 130 controls both emission source 110 and detector 120, and communicates with user interface 140. Each element will be described in greater detail below.

One or more of emission source 110, detector 120, controller 130, and user interface 140 may be cofabricated or colocated. In another embodiment, these elements may be fabricated and/or located separately.

Figure 2:
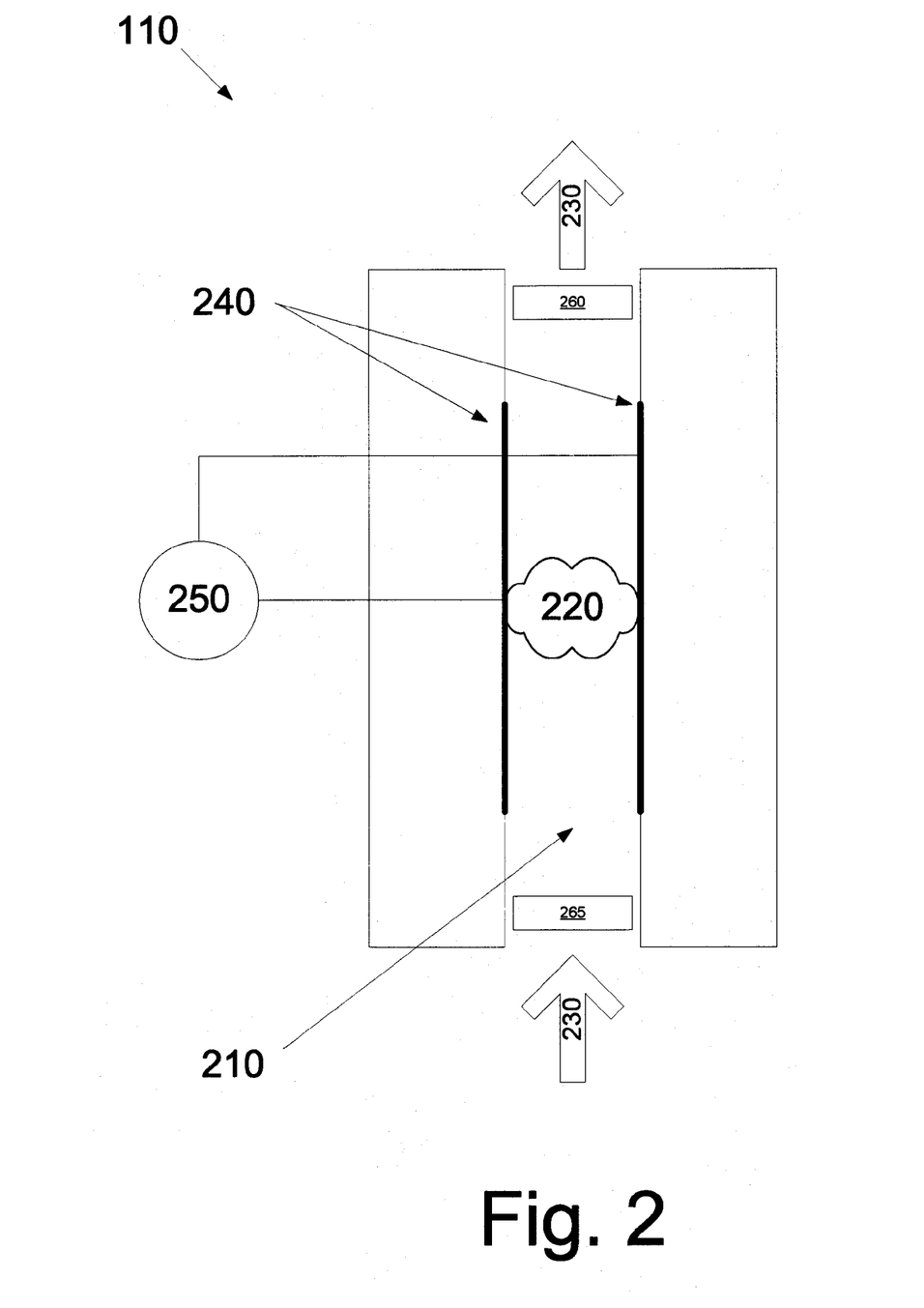
FIG. 2 is schematic of a microplasma conduit according to one embodiment of the present invention.

Referring to FIG. 2, a simplified schematic of emission source 110 according to one embodiment of the present invention is provided. Emission source 110 includes microplasma conduit, or conduit gap, 210 in which plasma 220 is developed. In one embodiment, microplasma conduit, 210 ranges in width from sub-microns to tens of tens of microns In a preferred embodiment, the width of microplasma conduit 210 is less than tens of microns.

Two ends of microplasma conduit 210 are open to allow a sample of gas or entrained gaseous mixture to enter at one end and exit at the other. An example gas flow is indicated by arrows 230.

Emission source 110 further includes conducting electrodes 240 that are disposed on opposite sides of conduit gap 210. In one embodiment, conducting electrodes 240 may be covered with a thin barrier layer (not shown). An example of a thin barrier layer would is barium titanate. Voltage source 250 applies to conducting electrodes 240 a voltage sufficient to produce an electric field. Examples of suitable voltage sources include Ultravolt model 1AA24, available from Ultravolt, Inc. Ronkonkoma, N.Y. 11779. An example suitable voltage range is between 0 and 1000 Volts. In one embodiment, a voltage source with a variable output voltage, such as the Ultravolt 1AA24, is useful because the breakdown voltage required to create plasma depends on a number of factors including sample gas composition, electrode material, electrode configuration, etc. The electromagnetic field creates glow discharge 220.

In one embodiment, the electric field may be direct. In another embodiment, the electric field may be alternating. In one embodiment, an alternating electric field may be modulated. This may be performed in order to reduce signal noise to detector 120.

The use of micro-systems technology to manufacture emission source 110 of the present invention provides several advantages over conventional devices. In one embodiment, emission source 110 and detector 120 may be delivered on a single, integrated platform. Due to this size, system 100 may be provided in a handheld device.

In addition, because the emission source of the present invention may be created using a process that is similar to integrated circuit processing, multiple sophisticated devices with demanding tolerances, and three dimensional forms, may be made simultaneously. In one embodiment, this may range to manufacturing thousands to millions of devices simultaneously. This allow for efficient manufacture of the emission source. Moreover, mixed functionality (electronics, sensing, optics, etc) may be realized on one common base, offering tiny systems with automatic self-referenced alignment, and robustness.

In one embodiment, emission source 110 may be manufactured as a replaceable cartridge.

On-chip optical detection permits a wide variety of gaseous species to be measured quickly, accurately and cheaply because optical alignment issues do not have as great of an impact as they would in a macrosystem. With on-chip optical detection, the pathlength the emitted light has to travel from the emission source to the detector is small. For example, the pathlength may be about 1 mm or less. This short pathlength permits all of the emitted light to reach the detector, thereby providing a strong signal. In a macrosystem counterpart, the pathlength may be from tens to hundreds of centimeters. Due to this length, mirrors are typically used to reduce the footprint of the pathlength. The inclusion of mirrors requires careful alignment to ensure that all the light is directed to the detector. Such alignment is very susceptible to vibrations and mechanical shock, typically requiring a work surface that is relatively immune from such interferences. Even so, regular checking of the alignment is required for optimal operation.

According to one embodiment of the present invention, emission source 110 may be operated as a series of optical resonant cavities, tuned for a particular constituent of the sample by a plurality of partially transmitting mirrors 260, 265 disposed oppositely on opposing sides of conduit 210 and perpendicular to the plane of conducting electrodes 240 and perpendicular to the plane of gas flow 230. The optical resonant cavity causes light of a particular wavelength, for example $\lambda_i$, to be reflected a large number of times, leading to an increase in the signal-to-noise ratio. This leads to an increase in sensitivity in the detection of the species of interest. The two partially transmitting mirrors are separated by a distance l, which defines the length of the optical cavity. The partially transmitting mirrors have a reflectivity close to one. In one embodiment, the reflectivity may be 0.995, meaning that 99.5% of incident light striking the mirror is reflected. The number of modes of the cavity is given by the relationship $l \approx n \cdot \lambda_i / 2$.

In another embodiment, an additional sensor, such as electrochemical cell 160, may be provided for calibration of detected light emission. An output signal from the electrochemical cell 160 may serve as secondary input to controller 130 to provide a reference signal for output from detector 120 for calibration.

Figure 6:
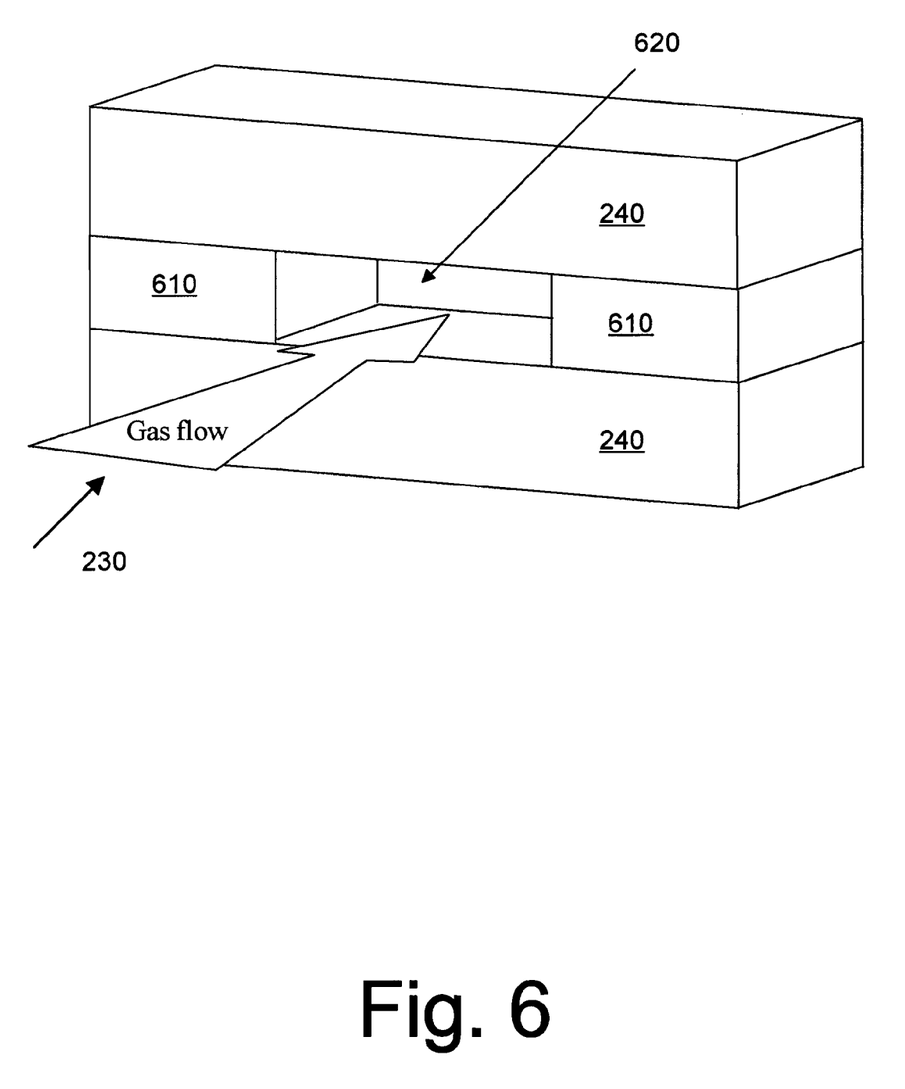
FIG. 6 is a schematic of a spacer according to one embodiment of the present invention.

In one embodiment, emission source 110 may act as a waveguide for the light from the conduit. Referring to FIG. 6, in one embodiment, emission source 110 may include spacer 610 that separates electrodes 240 from at a fixed distance from each other. In one embodiment, spacer 610 may include passage 620. In one embodiment, passage 630 may be in a center portion of spacer 610. Passage 630 permits gas to flow in a direction that is perpendicular to spacer 620 and parallel to electrodes 240.

In order for light to be transmitted from conduit 210 to detector 120, spacer 610 may be made of a material that is suitable for the transmission of electromagnetic energy in the wavelength range of interest. In one embodiment, spacer 610 may be made of polymethyl methacrylate (PMMA). In another embodiment, spacer 610 may be made of fused silica. Spacer 610 may not only function to separate electrodes 240, but to guide light from conduit 210 to detector 120. Spacer 610 may render unnecessary additional auxiliary items, such as an optical fiber, fiber bundle, etc.

Referring again to FIG. 1, in one embodiment, detector 120 is placed directly above emission source 110 to collect the spectrum of light emitted by plasma 220. In another embodiment, detector 120 may be located remotely from emission source 110, and may use a fiber optic (not shown) or fiber optic bundle (not shown) to deliver the emitted light from emission source 110 to detector 120.

In one embodiment, optical window 150 may be provided and located directly above the microplasma conduit. One suitable material for the window is magnesium fluoride. In one embodiment, window 150 may have a limited spectral range, for example, of 200 nm to 6 μm, with 80% or greater transmission. Other window materials and properties thereof may be used as necessary and/or desired.

Detector 120 is preferably an optical detector that is capable of responding to a portion of the wavelength range of the emitted light. Detector 120 may be a single unit, or it may include multiple units operating in series or in parallel. Peaks and bands in the measured spectrum characteristic of the emission spectra of a constituent, or more than one constituent, of the sample are identified with the detector's associated electronics.

In one embodiment, detector 120 may include a charge coupled device (CCD) and a monochromator. An example of a suitable CCD device is a liquid nitrogen-cooled, silicon-array detector, such as the Spectrum One-F24 detector, available from Horiba Ltd. This CCD device has a 512×512 pixel array and a spectral range of 300 nm to 1100 nm. An example of a suitable monochromator is the TRIAX 320, also available from Horiba Ltd. This monochromator has three different diffraction gratings: 1800 g/mm, 1200 g/mm and 300 g/mm. The resolution for the 1200 g/mm grating is 0.06 nm.

In another embodiment, detector 120 includes a photodiode or photodiode array that may be provided with a filter. Example filters include a narrow bandpass filter and a narrow bandpass filter wheel. A dispersion element, such as a Row-and circle or diffraction grating, may also be provided.

In still another embodiment, detector 120 may be a spectrometer.

Controller 130 may be provided to control emission source 110, detector 120, and user interface 140. In one embodiment, controller 130 may be a microprocessor-based controller. Controller 130 may perform several functions, including regulating power provided to emission source 110, and controlling the operation of detector 120. Controller 130 may control multiple emission sources 110, detectors 120, and/or user interfaces 140.

In one embodiment, controller 130 may process signals received from detector 120 and provide output for user interface 140. In one embodiment, the signal processing involves determining the relative intensities and wavelengths of the measured signals and, through comparison against a library database or pre-set, known reference points, identification of components in the gas sample. In an embodiment where a plurality of detectors 120 are networked, controller 130 may process signals for multiple detectors 120.

In another embodiment, controller 130 may store signals for later retrieval by a separate device.

In one embodiment, controller 130 may provide feedback to detector 120. Specifically, the light intensity of a characteristic peak or peaks of a particular constituent in the sample may be provided as feedback to the applied electric field in order to increase the signal-to-noise ratio for said particular constituent or to control the electron temperature of the plasma or to control heat dissipation within the conduit. For example, the amplitude of any prominent peak is a measure of the intensity of light emitted for that particular electronic transition, and is an indication of the rate of that particular electronic transition. The rate of that electronic transition is directly dependent on the concentration of the species involved for that transition, the concentration of electrons in the plasma and the mean electron energy (or temperature). Changing the mean electron temperature or changing the applied electric field to the plasma conduit will change the relative rates of the numerous electronic transitions occurring, causing transitions that were previously not favored to become favorable transitions, and vice-versa.

The use of feedback moves from an operating regime where detection of a species of interest is hampered by low signal-to-noise ratio to one where the characteristic electronic transitions for the species of interest is well defined.

The energetic processes occurring within the plasma and their evolution of heat may lead to thermal issues such as partial expansion of the emission source or localized micro-melting of the electrodes, controlling the mean electron temperature of the discharge. Thus, feedback may be used to control the generation of heat within conduit 120.

User interface 140 may be provided to provide the user with information concerning the operation of the sensor. In one embodiment, user interface 140 may include a display that displays the type of compound detected by detector 120. In another embodiment, user interface may provide an amount of the compound detected.

User interface 140 may also include an alarm, such as an audible or visual alarm, that may be activated when a certain compound or threshold of a compound is detected. User interface 140 may include an input device, such as a keypad, that allows a user to set the compound or threshold required to be detected before activating the alarm.

In one embodiment, user interface 140 may include a communications port (not shown) that allows for programming or downloading of data from user interface 140. User interface 140 may also be provided with a port that allows for wired or wireless (e.g., RF, microwave, etc.) communication over a network, such as the Internet.

Similarly, controller 130 may include a communications port that allows multiple sensors to function as a sensor array. This array of sensors may be capable of measuring and monitoring indoor air quality in a number of rooms, or an entire building. In such an embodiment, user interface 140 may monitor multiple controllers 130/detectors 120/emission sources 110.

Figure 3:
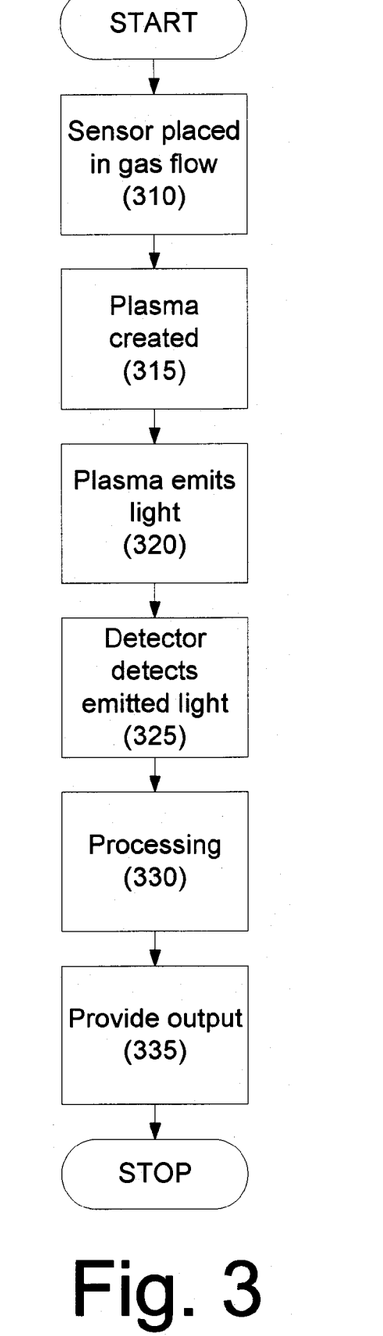
FIG. 3 is a flowchart depicting a method for measuring air quality using micro-optical mechanical gas sensor according to one embodiment of the present invention.

Referring to FIG. 3, a method for measuring air quality using micro-optical mechanical gas sensor is disclosed. In step 310, a micro-optical mechanical gas sensor is placed in a gas flow. In step 315, an electric field is applied across the electrodes and acts on the gas sample in the conduit, creating a plasma.

In step 320, the plasma discharge emits light. In step 325, the detector then detects the emitted light, and then in step 330, the detected spectrum is analyzed to determine the constituents of the gas. In one embodiment, a single constituent is identified by the detector. In another embodiment, more than one constituent is identified by the detector.

In step 335, output is provided by, for example, a user interface.

Emission source 110 may be manufactured by microfabrication techniques involving etched patterning of multi-layered materials. Referring now to FIGS. 4a to 4e, in FIG. 4a, silicon wafer 400 with a thin layer of silicon dioxide 420 is used as the substrate upon which the emission source is built. Silicon dioxide layer 420 improves the electrical insulation of substrate 410. Such wafers are readily available commercially. A layer of photoresist 430 is deposited, by spinning, on to the substrate, followed by baking, to drive off the solvent in the photoresist.

Figure 4A:
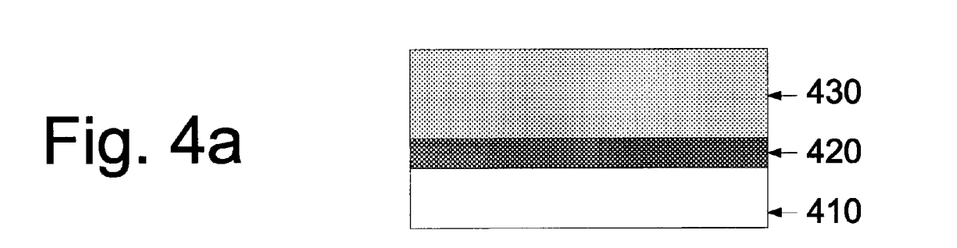
FIGS. 4a to 4e are schematics of a method for creating a micro-optical mechanical gas sensor according to one embodiment of the present invention.
Figure 4B:
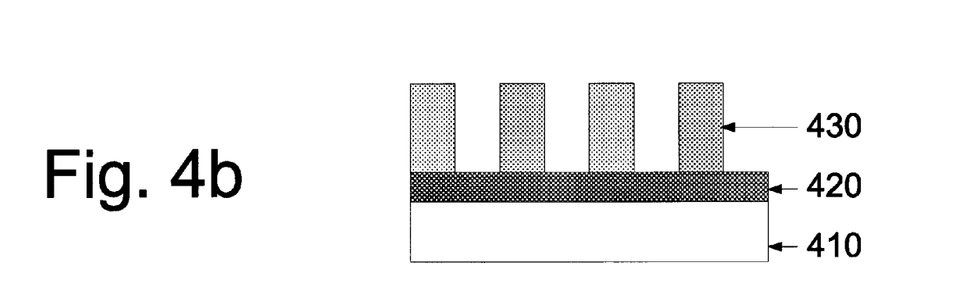
Figure 4C:
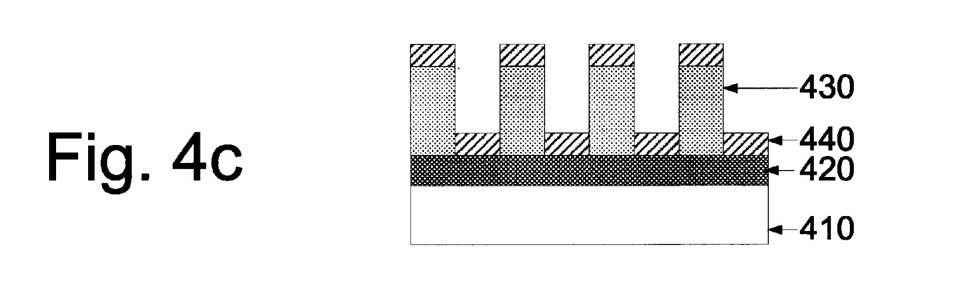

In FIG. 4b, masked etching is used to mark out the desired electrode pattern. A mask (not shown), custom-made commercially, consisting of chromium deposited on a glass substrate with the desired pattern etched by electron-beam technique is placed on top of photoresist layer 430 prior to etching. Etching, by photolithography, removes exposed photoresist 430. The mask is removed and, in FIG. 4c, a thin layer (approximately 20 nanometers thickness) of chromium 440 is deposited, to improve conduction.

Figure 4D:
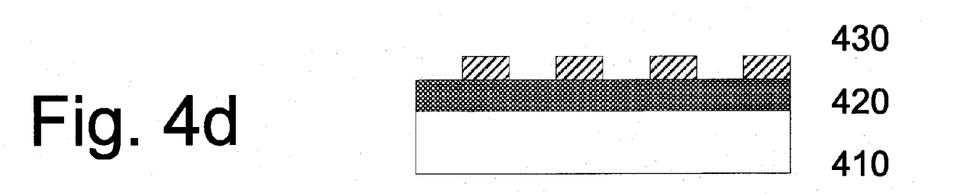
Figure 4E:
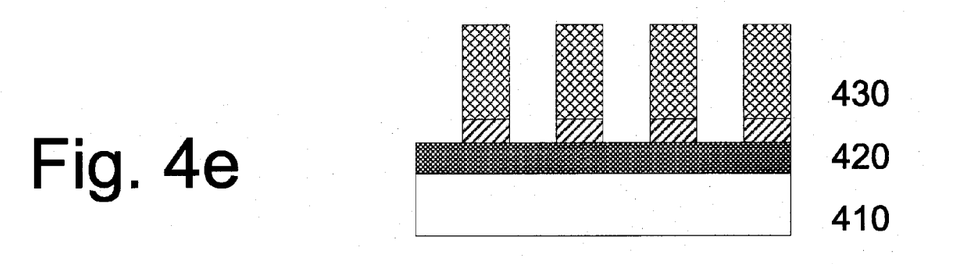

In FIG. 4d, the unit is dipped in developer which removes the resist ("lift-off"), leaving the intended electrode pattern. In FIG. 4e, electroplating allows building electrodes 450 to the desired height. In one embodiment, the height electrodes 450 may be up to approximately 20 microns.

Figure 5:
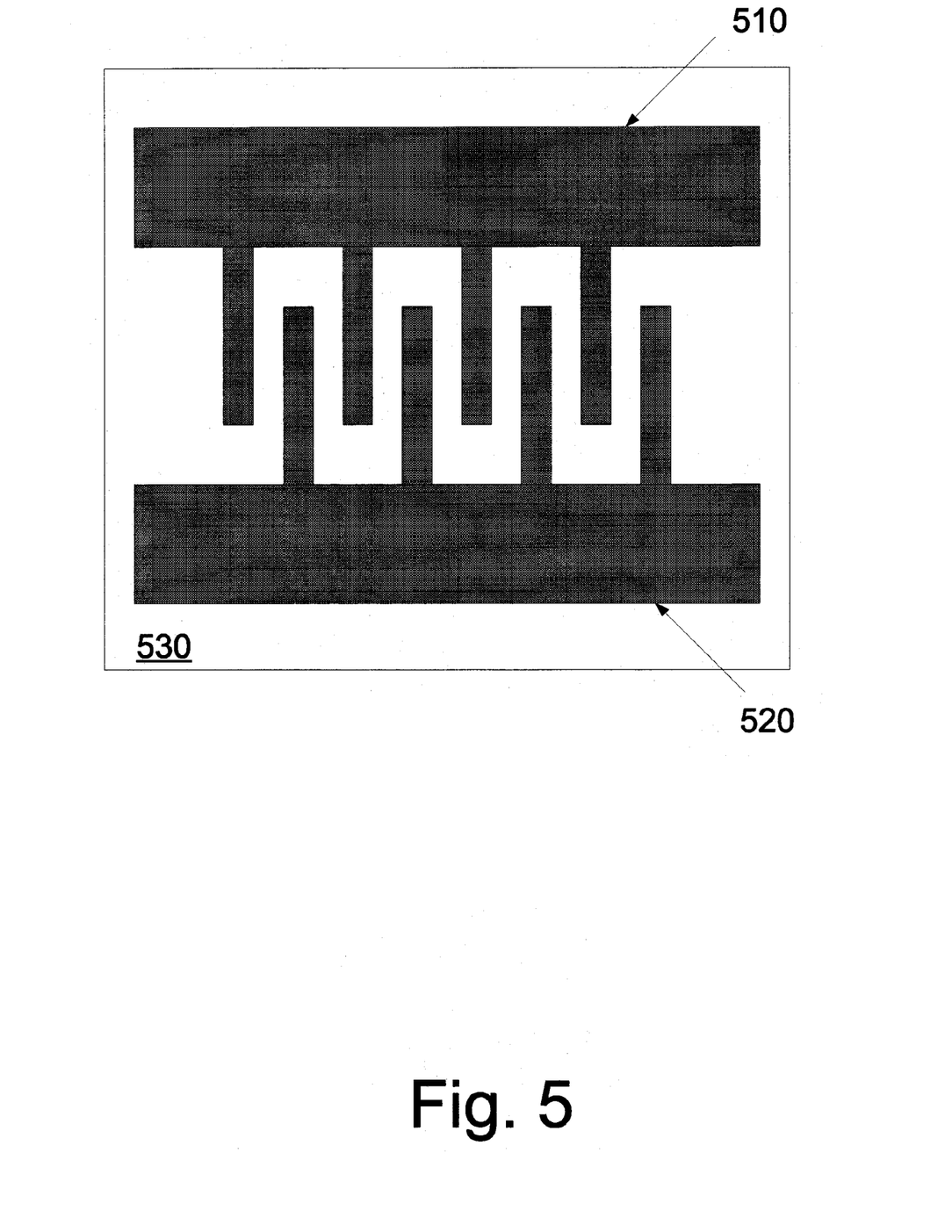
FIG. 5 is a schematic of a microplasma conduit according to one embodiment of the present invention.

Referring to FIG. 5, a plan view of a microplasma conduit in emission source 500 according to one embodiment of the present invention is illustrated. Electrode 510 is the positive electrode, electrode 520 is the negative electrode. Electrodes 510 and 520 are formed on substrate 530.

Other embodiments, uses, and advantages of the present invention will be apparent to those skilled in the art from consideration of the specification and practice of the invention disclosed herein. The specification and examples should be considered exemplary only.

What is claimed is:

1. A system for determining at least one constituent in an ambient gas, comprising:
    an emission source comprising:
    a conduit gap for receiving a natural flow of an ambient gas without mechanical assistance;
    a plurality of electrodes for applying an electric field to at least a portion of the conduit gap, the application of the electric field creating a microplasma in the conduit gap;
    a detector that detects an emission from the microplasma; and
    a controller that receives a signal from the detector and processes the signal to determine at least one constituent in the ambient gas;
    wherein the emission source and the detector are micro-optical mechanical devices.

2. The system of claim 1, wherein the width of the conduit gap is less than 100 microns.

3. The system of claim 1, wherein the width of the conduit gap is less than 10 microns.

4. The system of claim 1, wherein the detector is at least one of an optical detector, a charge coupled device, a photodiode, and a spectrometer.

5. The system of claim 1, wherein the emission source and the detector are located on the same chip.

6. The system of claim 1, wherein the emission source further comprises:
    a plurality of partially transmitting mirrors provided in the conduit gap.

7. The system of claim 1, wherein the emission source further comprises:
    a spacer having a passage within the conduit gap.

8. The system of claim 1, wherein the controller controls the emission source and the detector.

9. The system of claim 1, further comprising a spacer in the conduit gap.

10. A method for determining at least one constituent in an ambient gas, comprising:
    placing a chip containing an emission source and a detector in a natural flow of an ambient gas, the natural flow of the ambient as received without mechanical assistance;
    applying an electric field to at least a portion of a conduit gap within the emission source, the electric field creating a microplasma;
    detecting an emission from the microplasma; and
    processing data related to the detected emission to determine at least one constituent in the ambient gas.

11. The method of claim 10, wherein the emission source and the detector are a micro-optical mechanical devices.

12. The method of claim 10, wherein the width of the conduit gap is less than 100 microns.

13. The method of claim 10, wherein the width of the conduit gap is less than 10 microns.

14. The method of claim 10, wherein the step of detecting an emission from the microplasma comprises:
    detecting the emission with at least one of an optical detector, a charge coupled device, a photodiode, and a spectrometer.

15. The method of claim 10, further comprising:
    altering a strength of the electric field based on the detected emission.

16. The method of claim 10, further comprising:
    displaying an identity of the at least one constituent.

17. A system for determining at least one constituent in an ambient gas, comprising:
    a controller;
    a plurality of micro-optical mechanical sensor in communication with the controller, each micro-optical mechanical sensor comprising:
    an emission source having a conduit gap for receiving a natural flow of an ambient gas without mechanical assistance, a plurality of electrodes for applying an electric field to at least a portion of the conduit gap, the application of the electric field creating a microplasma in the conduit gap; and
    a detector that detects an emission from the microplasma;
    wherein the controller receives a signal from each of the detector and processes the signals to determine at least one constituent in the ambient gas received at each detector.

18. The system of claim 17, wherein the width of the conduit gap is less than 100 microns.

19. The system of claim 17, wherein the width of the conduit gap is less than 10 microns.

20. The system of claim 17, wherein the detector is at least one of an optical detector, a charge coupled device, a photodiode, and a spectrometer.

21. The system of claim 17, wherein the emission source and the detector are located on the same chip.

* * * * *